United States Patent
Snabre et al.

(10) Patent No.: US 7,782,458 B2
(45) Date of Patent: Aug. 24, 2010

(54) METHOD AND DEVICE FOR THE ANALYSIS OF MOVEMENT IN A SCATTERING MEDIUM

(75) Inventors: Patrick Snabre, Gradignan (FR); Laurent Brunel, Peyrins (FR)

(73) Assignee: Formulaction, L'Union (FR)

( * ) Notice: Subject to any disclaimer, the term of this patent is extended or adjusted under 35 U.S.C. 154(b) by 835 days.

(21) Appl. No.: 10/571,673

(22) PCT Filed: Sep. 24, 2004

(86) PCT No.: PCT/FR2004/002408
§ 371 (c)(1),
(2), (4) Date: Feb. 5, 2007

(87) PCT Pub. No.: WO2005/031324
PCT Pub. Date: Apr. 7, 2005

(65) Prior Publication Data
US 2008/0043233 A1    Feb. 21, 2008

(30) Foreign Application Priority Data
Sep. 25, 2003   (FR) .................................. 03 11218

(51) Int. Cl.
*G01N 15/02* (2006.01)
*G01N 21/00* (2006.01)
(52) U.S. Cl. ....................... 356/336; 356/337
(58) Field of Classification Search .......... 356/335–344
See application file for complete search history.

(56) References Cited

U.S. PATENT DOCUMENTS

| | | | | |
|---|---|---|---|---|
| 3,809,480 | A * | 5/1974 | Somerville et al. | 356/338 |
| 4,629,319 | A * | 12/1986 | Clarke et al. | 356/237.2 |
| 4,979,818 | A * | 12/1990 | Kobayashi | 356/28 |
| 5,274,361 | A * | 12/1993 | Snow | 345/166 |
| 5,561,515 | A * | 10/1996 | Hairston et al. | 356/28 |
| 6,034,760 | A * | 3/2000 | Rees | 356/28.5 |
| 7,227,531 | B2 * | 6/2007 | Lutian | 345/163 |
| 2003/0042304 | A1 * | 3/2003 | Knowles et al. | 235/384 |

FOREIGN PATENT DOCUMENTS

| | | |
|---|---|---|
| EP | 1 209 443 | 5/2002 |
| WO | WO 02/103332 | 12/2002 |

* cited by examiner

*Primary Examiner* — Gregory J Toatley, Jr.
*Assistant Examiner* — Jarreas C Underwood
(74) *Attorney, Agent, or Firm* — Young & Thompson

(57) ABSTRACT

Method and device for detecting and analyzing movement in a scattering medium, by: projecting a coherent light towards the scattering medium; performing a spatial and temporal sampling of the electromagnetic field of scattered light, in order to obtain a plurality of images of the electromagnetic field; and analyzing the speckle grains resulting from the images obtained from the spatial and temporal sampling of the electromagnetic field of the scattered light, in order to detect and analyze a movement in the scattering medium, the speckle grain analysis step including a step of analyzing the inter-image distance.

20 Claims, 2 Drawing Sheets

METHOD AND DEVICE FOR THE ANALYSIS OF MOVEMENT IN A SCATTERING MEDIUM

The present invention relates to a method of analysing movement in a scattering medium, and also to a device which makes it possible to implement said method.

Such a method and device are known in the prior art. In particular, the Applicant has disclosed methods and devices for analysing the phases of a multiphase mixture, which make it possible in particular to detect and measure the phenomena arising from particle segregation or sedimentation in mixtures as a function of time, for example emulsions or suspensions. The fields of application of these methods and devices include in particular the chemical and parachemical industry, and in a wider sense all fields in which it is necessary to analyse the structure and stability of a multiphase mixture or to detect the structure of a mixture or more generally of a scattering medium. The device for analysing the phases of the mixture comprises means for detecting electromagnetic radiation that is backscattered by the mixture, for example comprising photodiodes. Although such methods and devices work perfectly well, they require a considerable amount of time for acquiring the data needed for the analysis, and in some cases this time requirement may be high compared to the rate of evolution of the medium to be analysed, to the point of limiting the uses of these methods and devices.

The Applicant has also developed methods and devices which make it possible to measure a luminous flux which is for example backscattered by a scattering medium onto a receiver, and to measure this from the backscattering spot which is at least partly imaged onto the receiving means, said receiving means generally consisting of a matrix sensor, a CCD camera or a CMOS camera extending for example over a defined surface between two directions converging at the luminous barycentre of the backscattering spot. Such methods and devices make it possible to measure a spatial sampling of a profile of the luminous flux in the backscattering spot thus obtained. In this case, too, a large number of data acquisitions are required in order to obtain the measurements and results deriving therefrom.

In the prior art, there are also conventional methods for analysing movement in a scattering medium, based on studying the evolution over time of the electromagnetic field at one point in space, represented by a pixel, scattered by the scattering medium under the effect of injecting a coherent light into the latter. The electromagnetic field is sampled temporally while observing the Shannon criterion, that is to say a sampling frequency that is at least twice as high as the maximum frequency of the signal detected. If the number of samples is sufficient, a temporal auto-correlation function can be extracted with a Fourier analysis, for example. This is usually quite long in the case of small movements in the scattering medium, since, in order to reduce the measurement noise, it is necessary to find the mean of successive auto-correlations. Therefore, these methods and devices make it necessary to carry out a large number of acquisitions and averaging operations in order to obtain an auto-correlation or a spectrum of sufficient quality.

Document EP 1 209 443 is known, which relates to a method for image pick-up of a speckle grain pattern generated by a reflected light of a laser beam, and for analysing coagulation or fusion by using a pair of images which are compared successively, between one image and the image which immediately precedes it, so as to calculate a degree of coincidence such that a drying rate or a hardening rate obtained on the basis of this degree of coincidence can be displayed.

Document WO 02/103332 is also known, which relates to a method for measuring the properties of particles immersed in a body from a coherent light beam that is scattered by the particles. The speed of the particles can be analysed on the basis of the correlation between pairs of instantaneous images recorded at different moments, by using Fourier transform and the function of auto-correlation of the two starting images. Such a method uses inter-correlation analysis of images. It exhibits the drawback of having to multiply together the values of the pixels of each image one by one, which requires a considerable calculation time.

The present invention thus proposes a method and a device for analysing movement in a scattering medium, which permits a more rapid analysis and acquisition of the analysis data.

Another object of the present invention is to propose a method and a device for analysing movement in a scattering medium, which evolves more rapidly than the acquisition of the analysis data for the method and device of the prior art.

Another object of the present invention is to propose a method and a device for analysing movement in a scattering medium, which does not require precise positioning of the constituent elements with respect to one another, such as the light source, the medium to be analysed or the sensor.

More specifically, the invention relates to a method of detecting and analysing movement in a scattering medium, said method being characterised in that it consists in:
- projecting a coherent light towards said scattering medium;
- performing a spatial and temporal sampling of the electromagnetic field of the light scattered by said scattering medium, in order to obtain a plurality of images of said electromagnetic field; and
- analysing the speckle grains resulting from said images obtained from said spatial and temporal sampling of the electromagnetic field of the scattered light, in order to detect and analyse a movement in said scattering medium, characterised in that the speckle grain analysis step comprises a step consisting in analysing the inter-image distance.

The spatial and temporal sampling of the electromagnetic field of the light scattered by the scattering medium makes it possible to obtain speckle grain images which are representative with regard to the spatial sampling, at a given instant, of a state of the scattering medium, and representative in respect of the temporal sampling, of the evolution over time of the scattering medium, the latter optionally being a multiphase medium. Analysis of the inter-image distance makes it possible to define a temporal correlation time of the electromagnetic field, without however having to pass through a Fourier analysis.

According to another advantageous feature, the speckle grain analysis step comprises a step consisting in analysing part of the surface area of said images of said spatial sampling, and according to another feature, said part of the surface area of said images of said spatial sampling is equal to the surface of a speckle grain.

By passage into the frequency space, of the Fourier or wavelet type, this feature makes it possible to obtain a spectrum of the Doppler shifts and a characterisation of the movements of the microscopic structure of the scattering medium via the scattering coefficient or mean quadratic rate. Alternatively, it makes it possible to calculate the diameter of the particles.

According to another advantageous feature, the method according to the invention consists in determining the direction and speed of migration of all the speckle grains.

This feature derives from the inter-image distance analysis. If a movement in the scattering medium is taken into account, the direction of this movement corresponds, for example, to that of a chemical product which moves, flows, etc. Thus, with this analysis, two measurements are obtained: the correlation time and any direction and speed of movement.

According to another advantageous feature, the step consisting in projecting a coherent light towards said scattering medium consists in projecting a light beam having a diameter less than the free optical path length l* of the scattering medium.

This feature makes it possible to obtain a signal in the form of a plurality of photos, representing a spatial sampling at successive instants in a given lens.

According to another advantageous feature of the above, the speckle grain analysis step comprises a step consisting in carrying out a spatial auto-correlation of the successive images, and according to another advantageous feature, the method according to the invention consists in determining the profile of the backscattering spot.

This feature makes it possible to calculate the spatial intercorrelation of each image with itself. Another image is thus obtained which will have at its centre the mean speckle grain. Fourier transformation gives a relation between the size and shape of this mean grain and the size and shape of the aperture emitting the light, in this case the backscattering spot. There is thus provided a new means of obtaining the backscattering spot without imaging optics, but on condition of producing this spot by a suitable fine injection of coherent light as defined above.

According to another advantageous feature, the method according to the invention consists in analysing the evolution of the shape of said backscattering spot, in order to determine the probability of the scattering number.

This feature makes it possible, by obtaining the scattering coefficient or mean quadratic rate, to obtain a characterisation of the movements of the microscopic structure of the scattering medium or the diameter of the particles.

According to another advantageous feature, the method according to the invention consists in analysing the evolution of the size of said backscattering spot, in order to determine the free optical path length l* of the scattering medium and its evolution.

According to one advantageous feature, the speckle grain analysis step comprises a step consisting in separating the speckle grains according to the criterion of size and brightness.

Such a feature makes it possible to distinguish between the speed of particles included in and composing the scattering medium, for example close to the surface of the latter, and the speed of particles further away from the surface.

The invention also relates to a device for detecting and analysing movement in a scattering medium, characterised in that it comprises:

means for projecting a coherent light towards said scattering medium, matrix sensor means which can be used to perform a spatial and temporal sampling of the electromagnetic field of the light scattered by said scattering medium, in order to obtain a plurality of images of said electromagnetic field, means for observing said images of the electromagnetic field of the scattered light;

means for analysing the speckle grains resulting from said images; and means for analysing the inter-image distance.

Other features and advantages will emerge from reading the following description of several examples of embodiments of methods and devices according to the invention, accompanied by the appended drawings, said examples being given purely by way of non-limiting example.

FIG. 1 shows one application example of the method according to the invention, in which

Figure 1A:
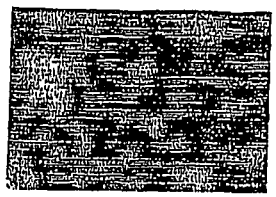
FIG. 1a is a representation of the speckle grains and FIG. 1b shows a diagram resulting from the analysis of the speckle grains.

A first example of embodiment of a method of detecting and analysing movement in a scattering medium consists in:

projecting a coherent light towards said scattering medium, by injecting a laser beam such that the impact of all the rays with the surface of the scattering medium covers a surface area which is not necessarily small with respect to the optical path length l* of the scattering medium;

performing a spatial and temporal sampling of the electromagnetic field of the light scattered by said scattering medium, in transmission or in backscattering depending on requirements, in order to obtain a plurality of images of said electromagnetic field, this step being able to be carried out by means of a matrix sensor from which a plurality of successive images can be collected, said images being or not being stored in a memory depending on requirements, for example depending on whether it is or is not possible to process the data in real time; each image is a spatial sampling of the strength of the electromagnetic field; the film constituting a temporal sampling of the evolution of the electromagnetic field over time; it is thus possible to configure this signal as a set of data items, each data item being coded in a three-dimensional space, namely two spatial dimensions X, Y and one time dimension; and analysing the speckle grains resulting from the images obtained from the spatial and temporal sampling of the electromagnetic field of the scattered light, in order to detect and analyse a movement in said scattering medium. The speckle grain analysis depends on the scattering medium analysed and on the aim of the analysis; several examples of analysis are given below as a function of particular application examples of the method according to the invention.

With regard to the analysis of the speckle grains, and in the case of spatial relation, it should be pointed out that, when a coherent light wave is injected into a scattering medium, it is possible to determine certain spatial characteristics of the electromagnetic field at a distance d from the scattering medium. Firstly, there is generally a scattering medium in the form of a volume, which permits the hypothesis that the phase of the wave arriving at the point of impact on the sampling means will have all the possible values, that is to say from 0 to $2\pi$. A speckle shape which is fully developed, that is to say with maximum contrast, is thus obtained. Moreover, in the absence of any optics influencing the propagation of the light between the scattering spot and the measuring sensor, the spatial auto-correlation of the speckle shape is the Fourier transform of the spatial auto-correlation of the light-emitting aperture, that is to say in our case the backscattering spot.

With regard to the analysis of the speckle grains, and in the case of temporal relation, it should be pointed out that the speckle shape is in fact the shape of interference produced by the scattering medium seen as an interferometer. In the case where the microscopic structure of the analysed scattering medium is moving, the speckle shape will also be moving. Pine and Maret, for example, published how to associate the movement of the particles with the variations in the electromagnetic field at a point in space; more specifically, they show how it is possible, from a particle movement model, to calculate the temporal auto-correlation function of the electromagnetic field at a certain point. This requires a large number of successive acquisitions in order to minimise noise, which takes a long time to carry out and thus prevents analysis of products with speed characteristics which change rapidly over time.

The speckle grain analysis step comprises a step consisting in analysing the inter-image distance. This method makes it possible to obtain an agitation measurement of the speckle in just a few images, which makes it possible, for example, to monitor products which dry very quickly. Two images can be seen as two points in a vectorial space, the size of which corresponds to the number of pixels of the matrix sensor used. In consideration of this, it is possible to define a vectorial distance between these two images: for example, as explained below with reference to FIG. 2 which shows one application example of the method according to the invention, the distance D2 is defined which is the square root of the sum of the squares of the differences between two values of the luminous intensity of two pixels of the same position in each image; as another example, it is possible to define the distance D1 which is the absolute value of the sum of the absolute values of the pixel-to-pixel differences, as with the distance D2. Then, a particular image in the film is selected, which thus corresponds to a given time. The distance of all the successive images with respect to this selected image is then calculated. The curve obtained of course starts around zero since the second image is the one which most resembles the reference image. It will converge towards a particular value which can be defined as the distance between two images which are completely different or decorrelated. Analysis of this curve will make it possible to define a temporal correlation time of our electromagnetic field, but this time without Fourier analysis.

The speckle grain analysis may comprise a step consisting in analysing the total surface area of the images of the spatial sampling. This analysis makes use of the property of ergodicity of the electromagnetic field. It should be noted that the noise is not reduced by a factor equal to the square root of the pixel number (when using a matrix sensor), but rather by a factor equal to the square root of the number of speckle grains. This is because statistical independence applies from one speckle grain to another but not from one pixel to another.

A first speckle grain analysis example may comprise, as an alternative to the above paragraph, a step consisting in analysing part of the surface area of the images of the spatial sampling, for example equal to the surface of a speckle grain, in particular after an analysis according to the speckle grain analysis described above.

It should be noted that it is possible to carry out an analysis of the similarity between at least two of the images. For example, an operator has subjected the scattering medium under analysis to some action or other; by analysing the similarity between the images of the speckle grains before and after the intervention, he can say whether the microstructure of the scattering medium has evolved or not. Any function of similarity between two images can be used, for example the function of distance between two images already mentioned above. It should be recalled that the microstructure concerned in the example is the distribution of the optical indices, real and imaginary, in space.

A second example of embodiment of a method of detecting and analysing movement in a scattering medium consists in:
  projecting a coherent light towards said scattering medium, by injecting advantageously a laser beam having a diameter of less than l*, that is to say less than the free optical path length of the scattering medium;
  performing a spatial and temporal sampling of the electromagnetic field of the light scattered by the scattering medium, as in the first example of embodiment of a method according to the invention described above; and
  analysing the speckle grains resulting from the images obtained from the spatial and temporal sampling of the electromagnetic field of the scattered light, in order to detect and analyse a movement in said scattering medium, by carrying advantageously out a spatial auto-correlation of the successive images. The spatial auto-correlation of the successive images which makes it possible to obtain via a new means the profile of the backscattering spot without imaging optics was explained above. The spatial auto-correlation of a speckle image in the case of fine injection of the laser makes it possible to know the probability of the number of scatterings and thus to obtain the particle scattering coefficient or the mean quadratic rate of the particles. For this, a speckle movement measurement is required, which is obtained by virtue of the inter-image distance. By virtue of the curve showing the evolution of the backscattering spot, it is possible to obtain in a known manner a measurement of the evolution of l* over time, for example in the case of applying a scattering medium to a non-absorbent chemical product (blank) or to a product whose absorption is known. It is thus possible, also in a known manner, to obtain the mean size of the scattering particles in the scattering medium where necessary, by using the Stokes-Einstein model which makes it possible to calculate the diameter on the basis of the scattering coefficient of the particles or to obtain the measurement of the light scattering capacity of a product, which is represented by the measurement of l*: this figure may make it possible for example to give covering or opacity power to a paint.

Knowledge of the profile of the backscattering spot makes it possible to analyse the evolution of the shape of the backscattering spot in order to determine the probability of the scattering number. Once injected into the scattering medium whose movement is to be analysed, each photon, in a conventional corpuscular model of light, will undergo a certain number of scatterings before re-emerging via the interface where it entered. A large number of photons will undergo a few scatterings to re-emerge immediately, the central part of the spot thus being very bright. A small number of said photons will undergo a large number of scatterings. Knowledge of the function of the probability of the number of scatterings associated with a movement model of the scattering structures makes it possible to calculate in a quantitative manner the movement of the particles and makes it possible to use the measurement of the electromagnetic variation obtained by virtue of the analysis using the inter-image distance. If the measurement obtained from the function of temporal auto-correlation in accordance with a method according to the invention is compared with that obtained by a conventional model either of particle scattering or of a particle convection movement, it is possible to obtain the main parameters of these models, that is to say the particle scattering coefficients and the mean quadratic rate of the particles. Two physical parameters which are important in terms of the hydrodynamics of fluids are thus obtained.

Referring now to the above-described first example of embodiment of a method according to the invention, the described speckle grain analysis examples make it possible, as seen above, to obtain an optical correlation time which is the time required for the electromagnetic field to be decorrelated with itself. The inverse of this time gives a measurement of the agitation rate of the analysed scattering medium. It is thus possible, for example, to apply such methods to the analysis of particle sedimentation, to the drying of a product, to the propagation of a liquid into a porous structure, and also to the calculation of the scattering coefficient. This is because, a paint which dries for example is a solution of particles in a solvent which evaporates; Brownian agitation of these particles will slow down as the solvent disappears; this slowing-down is thus monitored by virtue of the method according to the invention, and a drying curve, as a function of time, is thus obtained. In relation to the propagation of a liquid into a porous structure, the physical parameter which changes is the optical index. This is because a liquid which propagates into a porous structure, for example water which wets paper, will gradually replace the zones occupied by air (index=1) with zones occupied by water (index=1.33) or any other liquid. In this case, the method according to the invention makes it possible to use the movement of the speckle grains via the signal processing algorithms described above.

Still referring to the above-described first example of embodiment of a method according to the invention, the inter-image distance analysis, which likewise makes it possible to obtain the optical correlation time but also the direction and speed of migration of all the speckle grains, as explained below, finds application for example in studying the flow of scattering media by measuring a flow rate of a paint for example, based on the algorithm for measuring the direction and speed of the speckle grains, or else in analysing the migration of particles contained in a scattering medium and partly constituting the latter, or else in analysing the scattering of particles in a random network, for these two latter applications with the possibility of separating the speckle grains according to the criterion (size, brightness) as explained below. To measure a direction and a speed of the speckle grains, it is possible to use the inter-image distance as follows: this distance is calculated between a first image and a second image, but with the second image having been offset by one to several pixels in all possible directions. The shift which gives the minimum distance gives us a vector. The direction and norm of this vector give us the direction and speed of mean displacement of the speckle grains. The study of the migration of the particles is carried out on the basis of the algorithm for measuring the direction and speed of the speckle grains, measuring the speed of all the particles which are displaced without erratic movement with respect to one another. The study of the scattering of particles in a random network is carried out on the basis of the algorithm for measuring the direction and speed of the speckle grains and also the algorithm for measuring random displacements of the speckle grains, the method according to the invention furthermore making it possible to measure the movement of particles which are displaced in a fixed random structure, or porous structure, for example particles of ink which diffuse into paper.

Figure 1B:
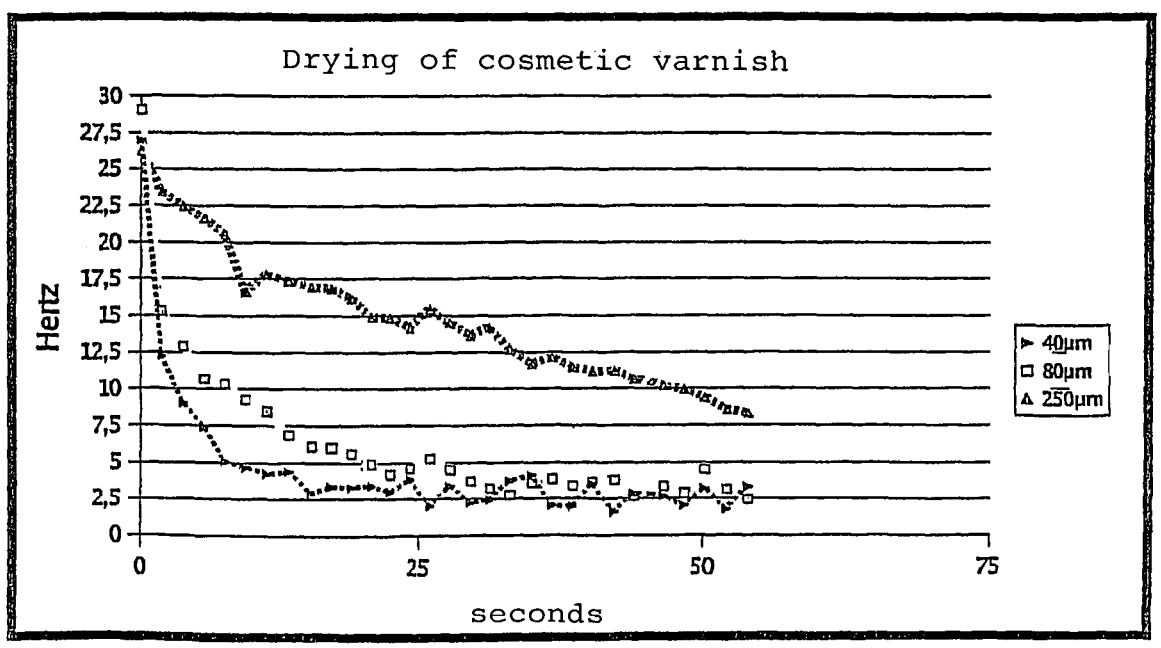

FIG. 1b shows an example of a paint or varnish drying curve obtained from the signal processing: inter-image distance D2 described above. The ordinate shows the inverse of the correlation time in Hertz, the abscissa shows the time in seconds. A slowing-down of the movement of the particles in the scattering medium can be seen, this being due to the evaporation of the solvent which gives rise to an increase in viscosity and thus a reduction in the scattering coefficient of the particles. The three curves correspond to different layer thicknesses of the scattering medium. It can be seen that the thicker the layer, the more time the medium takes to dry, that is to say to have its particles immobilised.

Another speckle grain analysis example which can be applied to the second example of the method described above may furthermore comprise a step consisting in separating the speckle grains according to the criterion of size and brightness. One application example of this type of analysis is the analysis of movement in a paint which dries to form a skin. The method makes it possible to distinguish between the speed of the particles which are close to the surface and the speed of the particles which are further away from this surface. For this, it should be recalled that, when light is injected onto the surface of a scattering medium, a backscattering spot forms; it is known that the centre of the spot, which is very bright and of small diameter (of the order of l*) essentially emits "short photons", that is to say photons which have penetrated the medium to a small depth (depth of the order of l*); it is also known that, consequently, the edge of the spot which is not very bright and is of large diameter (of the order of 10 to 100 times l*) essentially emits "long photons", that is to say photons which have penetrated the medium to a large depth (depth of the order of 10 to 100 times l*); it should be pointed out that a small bright spot will create speckle grains which are bright and of large size. Conversely, a large spot that is not very bright will create speckle grains which are of small size and not very bright. It can be deduced therefrom that the separate observation of the grains which are bright and of large size and of the grains which are not very bright and of small size will make it possible to separately measure the speed of displacement of the microscopic structure of the scattering medium at the surface and at depth. The application example described above confirms this: for a paint which dries and forms a skin on the surface, all the speckle grains can be seen moving at the start, then, little by little, the large bright grains become immobile before the small grains which are not so bright. At the end of the experiment, all the speckle grains are immobilised. It can thus be deduced therefrom that the paint dries firstly at the surface and then at depth. A signal processing operation can thus be envisaged which will separate categories of grains by the criterion (size, brightness), the small dark grains from the large bright grains and other intermediate categories. It is thus possible to produce as many new films for each category. To each category, it will again be possible to apply various processing operations, for example as indicated below, and thus to obtain no longer just a single measurement but rather a histogram of measurements.

Figure 2:
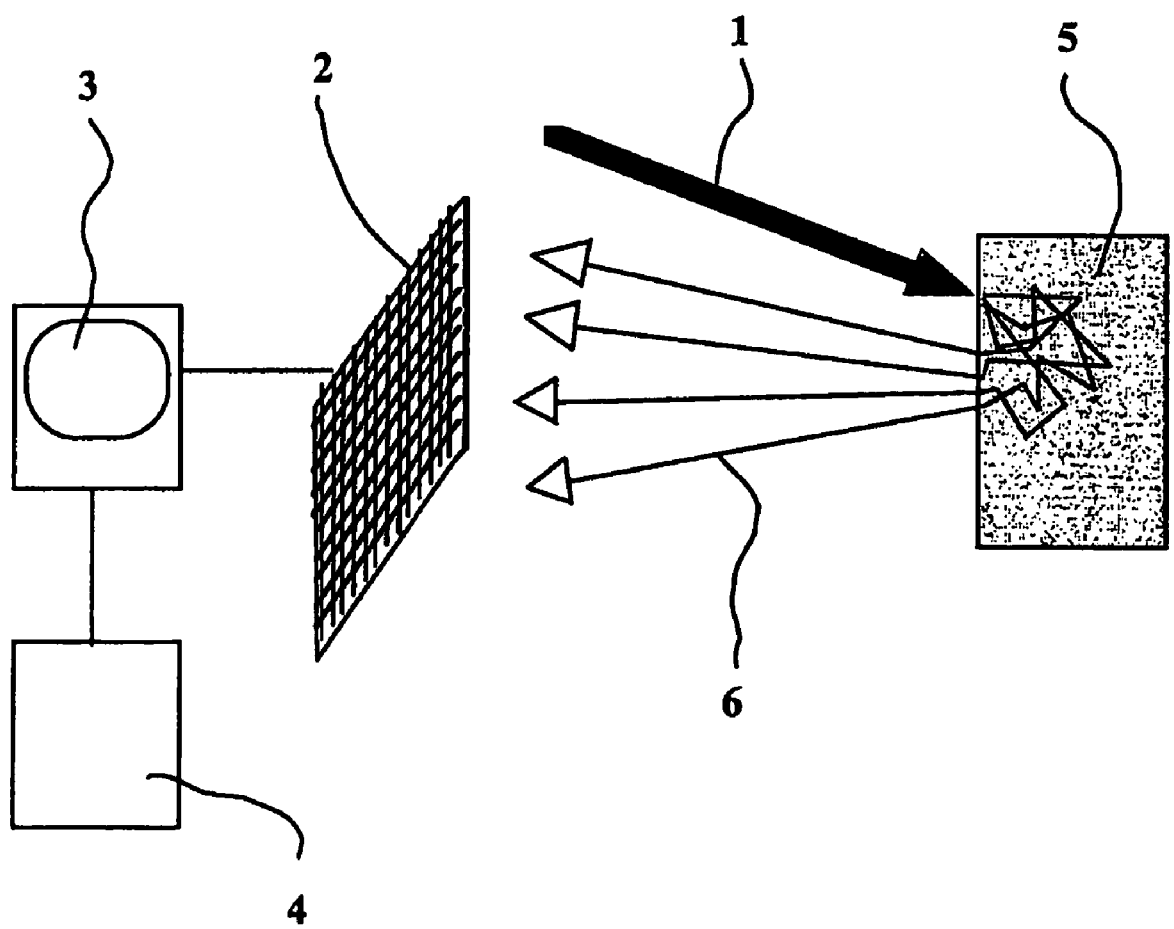
FIG. 2 shows a schematic view of one example of embodiment of a device for analysing movement in a scattering medium, according to the invention.

FIG. 2 shows a functional diagram of one example of a device for detecting and analysing movement in a scattering medium, which makes it possible to implement a method according to the invention for detecting and analysing movement in a scattering medium. The device comprises:

means 1 for projecting a coherent light towards the scattering medium 5, for example a laser beam, either by means of a conventional laser or by means of a laser diode, which can be used to inject into the scattering medium to be analysed a beam whose rays at the point of impact are less than l* or of the order of l*, matrix sensor means 2 which can be used to perform a spatial and temporal sampling of the electromagnetic field of the light 6 scattered by the scattering medium, in order to obtain a plurality of images of the electromagnetic field, for example a flat multi-pixel sensor, means 3 for observing the images of the electromagnetic field of the scattered light, for example a monitor which makes it possible to supply an imaged representation of the electromagnetic field, means 4 for analysing the speckle grains resulting from the images, which consist of calculation means that make it possible to carry out the speckle grain analyses described above. The calculation means will advantageously be embodied by a computer program, or by a wired logic implementation, for example FPGA or ASIC, or by on-board components, for example of the microprocessor type, and will comprise, depending on requirements, means for separating the speckle grains according to the criterion of size and brightness, means for analysing part of the surface area of the images of the matrix sensor, means for analysing the surface of a speckle grain, means for analysing the inter-image distance, means for calculating the direction and speed of migration of all the speckle grains, means for carrying out a spatial auto-correlation of the successive images, means for determining the profile of the backscattering spot, means for analysing the evolution of the shape of the backscattering spot in order to determine the probability of the scattering number, means for analysing the evolution of the size of the backscattering spot in order to determine the free optical path length l* of the scattering medium.

The invention claimed is:

1. Method of detecting and analyzing movement in a scattering medium, said method comprising:
   projecting a coherent light towards said scattering medium;
   performing a spatial and temporal sampling of the electromagnetic field of the light scattered by said scattering medium, in order to obtain a plurality of images of said electromagnetic field, said plurality of images providing a plurality of speckle grain images which are representative with regard to the spatial sampling, at a given instant, of a state of the scattering medium, and representative in respect of the temporal sampling, of the evolution over time of the scattering medium; and
   analyzing the speckle grains resulting from said images obtained from said spatial and temporal sampling of the electromagnetic field of the scattered light, in order to detect and analyse a movement in said scattering medium,
   wherein the speckle grain analysis step comprises a step consisting in analyzing the vectorial inter-image distance.

2. Method according to claim 1, wherein the speckle grain analysis step comprises a step of analyzing part of the surface area of said images of said spatial sampling.

3. Method according to claim 2, wherein said part of the surface area of said images of said spatial sampling is equal to the surface of a speckle grain.

4. Method according to claim 1, further comprising determining the direction and speed of migration of all the speckle grains.

5. Method according to claim 1, wherein the step consisting of projecting a coherent light towards said scattering medium comprises projecting a light beam having a diameter less than the free optical path length (l*) of the scattering medium.

6. Method according to claim 5, wherein the speckle grain analysis step comprises a step of consisting in carrying out a spatial auto-correlation of the successive images.

7. Method according to claim 6, further comprising determining the profile of the backscattering spot.

8. Method according to claim 7, further comprising analyzing the evolution of the shape of said backscattering spot, in order to determine the probability of a scattering number.

9. Method according to claim 7, further comprising analyzing the evolution of the size of said backscattering spot, in order to determine the free optical path length (l*) of the scattering medium and its evolution.

10. Method according to claim 5, wherein the speckle grain analysis step comprises a step of separating the speckle grains according to the criterion of size and brightness.

11. Device for detecting and analyzing movement in a scattering medium, which comprises:
    means (1) for projecting a coherent light towards said scattering medium (5),
    matrix sensor means (2) which can be used to perform a spatial and temporal sampling of the electromagnetic field of the light (6) scattered by said scattering medium, in order to obtain a plurality of images of said electromagnetic field, said plurality of images providing a plurality of speckle grain images which are representative with regard to the spatial sampling, at a given instant, of a state of the scattering medium, and representative in respect of the temporal sampling, of the evolution over time of the scattering medium,
    means (3) for observing said images of the electromagnetic field of the scattered light;
    means (4) for analyzing the speckle grains resulting from said images; and
    means for analyzing the vectorial inter-image distance.

12. Device according to claim 11, further comprising means for analyzing part of the surface area of said images of said spatial sampling.

13. Device according to claim 12, further comprising means for analyzing the surface of a speckle grain.

14. Device according claim 11, further comprising means for calculating the direction and speed of migration of all the speckle grains.

15. Device according to claim 11, further comprising means for projecting a light beam having a diameter less than the free optical path length (l*) of the scattering medium.

16. Device according to claim 15, further comprising means for carrying out a spatial auto-correlation of the successive images.

17. Device according to claim 16, further comprising means for determining the profile of the backscattering spot.

18. Device according to claim 17, further comprising means for analyzing the evolution of the shape of said backscattering spot, in order to determine the probability of the scattering number.

19. Device according to claim 17, further comprising means for analyzing the evolution of the size of said backscattering spot, in order to determine the free optical path length (l*) of the scattering medium.

20. Device according to claim 15, further comprising means for separating the speckle grains according to the criterion of size and brightness.

* * * * *